(12) United States Patent
Chui

(10) Patent No.: US 7,630,531 B2
(45) Date of Patent: Dec. 8, 2009

(54) ENHANCED NAVIGATIONAL TOOLS FOR COMPARING MEDICAL IMAGES

(75) Inventor: Haili Chui, Sunnyvale, CA (US)

(73) Assignee: MeVis Medical Solutions, Inc., Pewaukee, WI (US)

( * ) Notice: Subject to any disclaimer, the term of this patent is extended or adjusted under 35 U.S.C. 154(b) by 727 days.

(21) Appl. No.: 11/344,832

(22) Filed: Jan. 31, 2006

(65) Prior Publication Data

US 2007/0177780 A1  Aug. 2, 2007

(51) Int. Cl.
 *G06K 9/00* (2006.01)
(52) U.S. Cl. ..................................... 382/128
(58) Field of Classification Search ................. 382/128, 382/131; 600/437
 See application file for complete search history.

(56) References Cited

U.S. PATENT DOCUMENTS

2003/0016850 A1 * 1/2003 Kaufman et al. ............ 382/128
2003/0095697 A1   5/2003 Wood et al.
2006/0020205 A1   1/2006 Kamiyama

* cited by examiner

*Primary Examiner*—Bhavesh M Mehta
*Assistant Examiner*—Nirav G Patel
(74) *Attorney, Agent, or Firm*—Quarles & Brady LLP

(57) ABSTRACT

A navigation tool that provides a side-by-side display of two temporally related medical images of the same region of a patient. A plurality of lines extend between the images, at least a first line beginning at a feature at a first location in a first image and ending at a corresponding feature at a corresponding location in the second image and at least a second line extending from a feature found at a second location in one of the images toward a corresponding second location in the other image and indicating a feature found in one image but not the other. Preferably, the navigational tool also includes a scroll bar alongside the display of medical images. On the scroll bar are a series of markers, each marker corresponding to one of the plurality of lines that extend between the images and preferably being aligned with that line.

22 Claims, 4 Drawing Sheets

ENHANCED NAVIGATIONAL TOOLS FOR COMPARING MEDICAL IMAGES

BACKGROUND OF THE INVENTION

This relates to navigational tools to facilitate the comparison of two temporally related medical images on a computer-driven display. The term medical images is used broadly herein to refer not only to actual images such as x-rays, CT axial sections, MRI images, sonograms, mammograms and the like, but also to representations and/or abstractions of such images as in the case of a display of regions of interest on an anatomical background map. The invention is particularly useful in the comparison of chest computer tomography (CT) scans of the same patient taken at different times and will be described in that context. The principles of the invention may, however, be applied in the comparison of any two medical images of the same features.

It is common clinical practice to acquire chest CT scans of the same patient at different times and compare them to monitor nodular structures. By comparing the potentially pathological nodular structures present in these scans, vital diagnostic/treatment information can be obtained.

In today's clinical practice, the tracking and comparing of nodules across multiple temporal CT scans is a very tedious process. Modern CT scans produce image stacks of hundreds of axial image slices. While numerous tools exist for matching the major anatomical features of the lungs that are visible in both stacks, it is extremely time-consuming to find and match the corresponding nodules in the two stacks of hundreds of axial slices.

SUMMARY OF THE PRESENT INVENTION

The present invention is directed to a navigation tool that facilitates this matching and comparative visualization process. In an illustrative embodiment of the invention, the tool provides a side-by-side computer-driven display of two temporally related medical images of the same region of a patient. A plurality of lines extend between the images, at least a first line beginning at a feature at a first location in a first image and ending at a corresponding feature at a corresponding location in the second image and at least a second line extending from a feature found at a second location in one of the images toward a corresponding second location in the other image where no corresponding feature is found. Thus, the second line indicates a feature found in one image but not the other. If the feature is found in the first image in time but not the second, it has disappeared; and if the feature is found in the second image in time but not the first, it is new. Advantageously, the first and second lines have different visual appearance. For example, they are different colors.

In a preferred embodiment of the invention, the navigational tool also includes a scroll bar alongside the display of medical images. On the scroll bar are a series of markers, each marker corresponding to one of the plurality of lines that extend between the images and preferably being aligned with that line. By advancing a cursor to a marker and clicking a mouse button, the axial section or sections associated with the corresponding line are displayed.

Advantageously, the visual appearance of the markers varies with the lines with which they are associated. For example, they may have the same color as the line and that color may vary depending on whether the line joins features in the two images or the feature is found only in the first image in time or the second image in time. Alternatively, ;the marker can be a line whose length varies with the lines between the two images. For example, the marker line may be longest in the case where the associated line joins two features in the two medical images and the marker line may be only half that length where the line is connected to only one feature. Further, the position of the shorter marker line may be varied to indicate whether the feature it connects to is in the first image or the second image.

BRIEF DESCRIPTION OF THE DRAWINGS

These and other objects and features of the present invention will be more readily apparent from the following Detailed Description in which.

DETAILED DESCRIPTION

Figure 1:
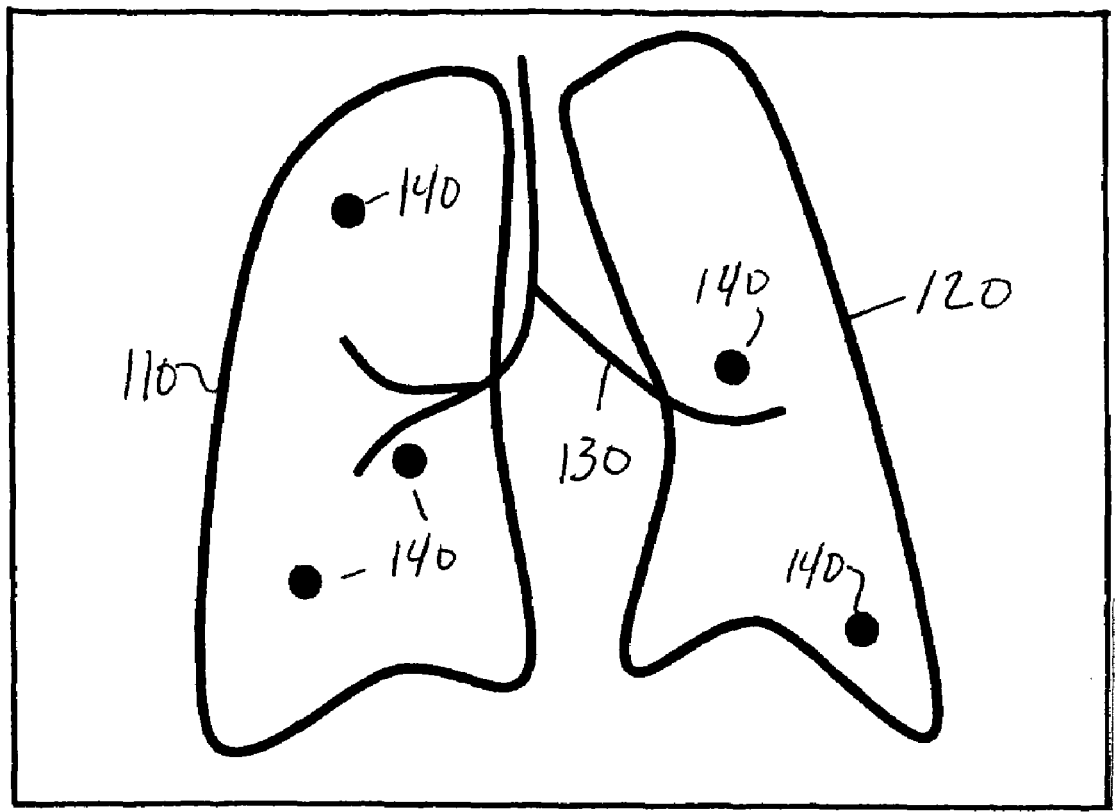
FIG. 1 is a schematic illustration of a display of nodules on a lung anatomical background map.

FIG. 1 depicts a display 100 of nodules on a lung anatomical background map constructed to facilitate localization and comparative visualization of the nodules. Using sophisticated image processing and segmentation tools, key anatomical structures can be extracted from the original x-rays, CT axial sections and the like and represented in a map in several ways. For example, one can project the anatomical structures onto a 2D plane and create a projection 2D map. Another method, as shown here, is to create a line drawing type of map to represent the lung anatomy. The border of the lungs is represented by closed lines 110, 120. Other anatomical background such as the airway and vascular structures are represented by dark lines 130. The approximate location of nodules relative to the background structures represented by lines 110, 120, 130 is shown by discs 140. Advantageously, the discs are brightly colored, e.g., red, to make them stand out in the display. Alternatively, the discs could blink or be emphasized in other ways. Advantageously, the size of the disc may vary in proportion to the size of the nodule.

The display of FIG. 1 has been successfully implemented in computer-aided nodule analysis software such as the assignee's ImageChecker® CT software and is referred to as a "nodule navigation map." Illustrative apparatus for the display of such map is described in detail in assignee's U.S. Pat. Nos. 6,925,200 for "Graphical User Interface for Display of Anatomical Information," which is incorporated herein in its entirety. With the major anatomical structures shown in the background, it is very easy to get a quick global visualization and understanding of important details of the whole case: how many nodules there are, where they are, how big they are and similar types of useful information. Moreover, each disc is advantageously hot-linked to the CT section that contains an image of the nodule it represents so that by aligning an indicating device such as a cursor with a nodule and activating a selection device such as a mouse, the radiologist can access the corresponding CT section. Thus, the map provides a convenient way for the radiologist to access the individual CT section that contains an image of the nodule.

As noted above, it is common clinical practice to acquire chest CT scans of the same patient at different times and to compare these scans to monitor nodular structures. Such comparison, however, requires the radiologist to navigate through two stacks of hundreds of axial image slices. Moreover, some benign nodules can decrease in size and eventually disappear from later scans while certain malignancies can spread and cause new modules to appear in later scans.

Figure 2:
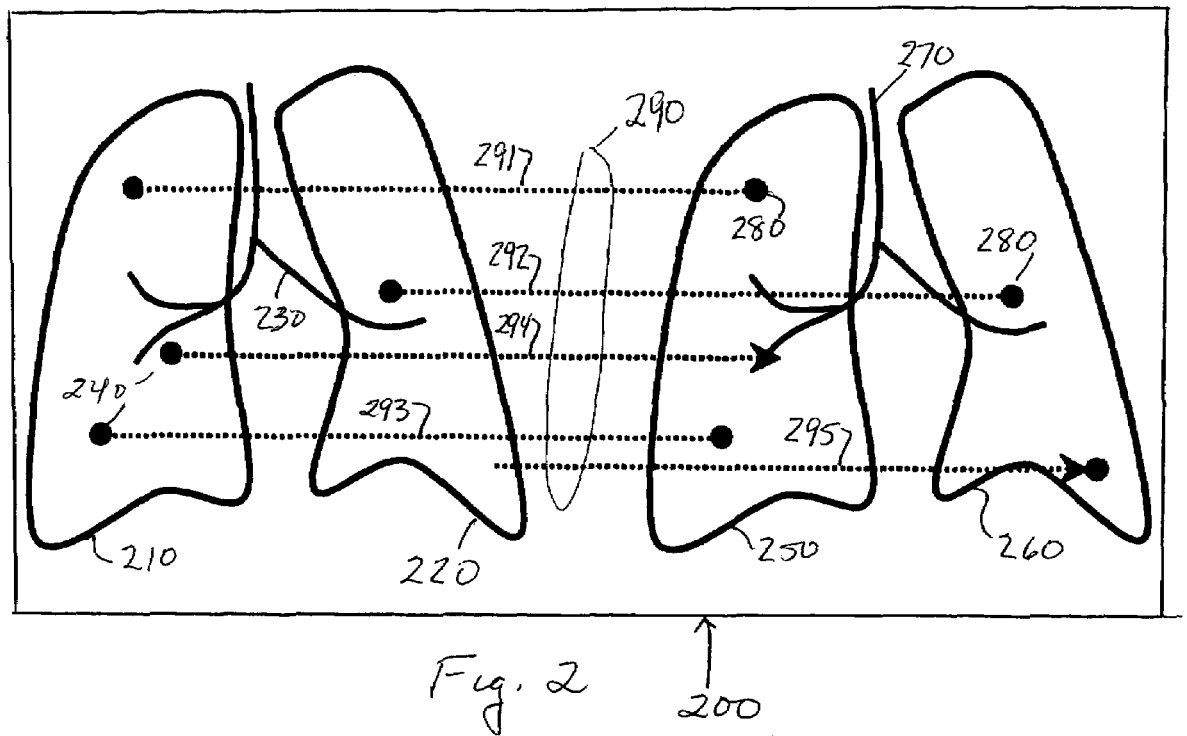
FIG. 2 is a schematic illustration of a display in a first embodiment of the invention.

One aspect of the present invention is a navigational tool that facilitates the comparison of two temporally related medical images on a computer screen or the like. FIG. 2 depicts a display 200 of two such images side-by-side. Again, the images depict nodules on a lung anatomical background map generated by nodule analysis software running on a computer system. Illustratively, the image on the right hand side is later in time. In the image shown on the left hand side, the border of the lungs is represented by closed lines 210, 220. Other anatomical background such as the airway and vascular structures are represented by dark lines 230. The approximate location of nodules relative to the background structures is shown by discs 240. In the image shown on the right hand side, the border of the lungs is represented by closed lines 250, 260 and other anatomical background by dark lines 270. The approximate location of nodules relative to the background structures is represented by discs 280.

In accordance with the invention, the software determines which nodules in one image correspond to those in the other image and generates a plurality of lines 290 that extend between the images. As shown in FIG. 2, some lines 291-293 begin at a disc 240 in the first image and terminate at a disc 280 at the corresponding location in the second image. Thus, these lines are associated with features found in both images. Another line 294 extends from a disc 240 in the first image toward the corresponding location in the second image but does not terminate at any disc in the second image. This line is associated with a feature found in the first image but not found in the second because it has disappeared. Another line 295 extends from a disc 280 in the second image toward the corresponding location in the first image but does not start from any disc in the first image. This line is associated with a feature found in the second image but not found in the first image because it is new.

Advantageously, the various lines 290 can have different colors or other distinguishing characteristics. For example, lines 291-293 linking discs in both images might be blue, line 294 relating to a disc that is not found in the second image might be green and line 295 relating to a newly found disc in the second image might be red.

Figure 3:
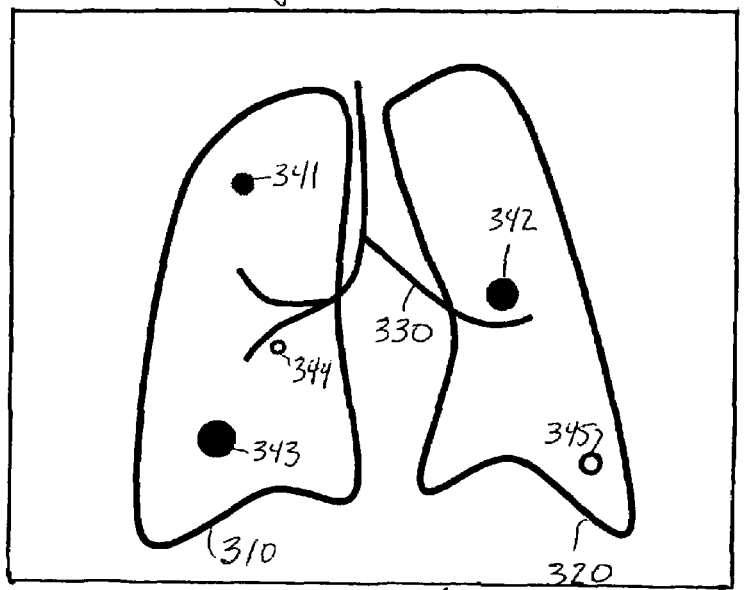
FIG. 3 is a schematic illustration of a display in a second embodiment of the invention.

The information in FIG. 2 may also be condensed into a display in a single image of the lungs in which different marker symbols are used to distinguish nodules that appear in both temporal images from nodules that appear only in the first image or only in the second image. FIG. 3 is a display 300 of such nodules on a lung anatomical background map. Again, the border of the lungs is represented by closed lines 310, 320 and the airway and vascular structure by lines 330. Nodules that are found in both sets of temporal images are represented by solid black discs 341, 342, 343. Nodules that are found in the first image but not the second are represented by a disc 344 of another color such as green; and nodules that are found in the second image but not in the first are represented by a disc 345 of still another color such as red. Other visually distinguishing characteristics may be used to distinguish the different kinds of nodules. In FIG. 3, for purposes of illustration, disc 344 is represented by a small circle and disc 345 is represented by a large circle.

Again, other marking arrangements can be used with or in place of the foregoing arrangements. For example, the size of the disc can be in proportion to the size of the nodule. New nodules might be indicated by a blinking disc. In addition, it may also be advantageous to indicate changes in size of the nodules by color coding or other arrangements. For example, numbers might be displayed alongside the disc indicating the percent change in the size of the nodule in the second image relative to the first. Plus and minus signs could be used to show the direction of change or colors such as red and green.

Figure 4:
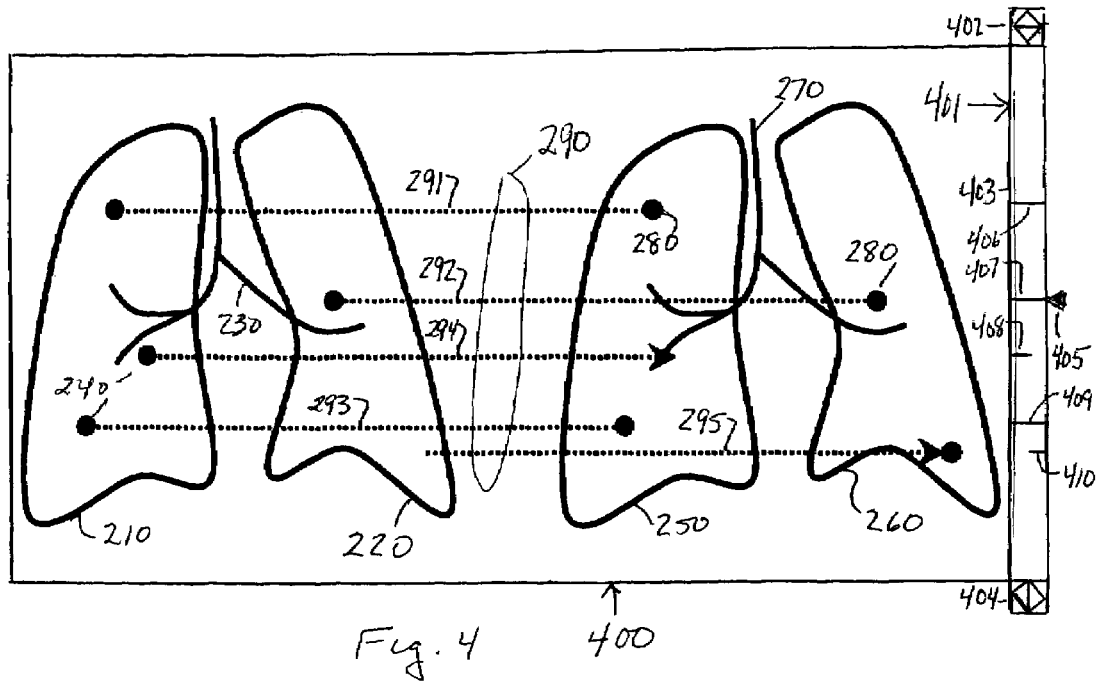
FIG. 4 is a schematic illustration of a first display in a third embodiment of the invention.

In a preferred embodiment of the invention, the navigational tool also includes a scroll bar on one side or the other of the display of medical images. FIG. 4 depicts a display 400 of two temporally related images with a scroll bar 401 along the right-hand side. The temporally related images are the same as those of FIG. 2. Accordingly, they have been numbered the same and will not be described further. Scroll bar 401 comprises a first set of up and down scroll buttons 402, a display bar 403, a set of left and right scroll buttons 404 and a cursor 405. On the scroll bar are a series of horizontal lines or markers 406-410, each of which corresponds to one of the plurality of lines that extend between the pair of medical images to the left of the scroll bar. Preferably, each marker is aligned with its corresponding line between the pair of images. Since each nodule in the images also is found in one of the CT axial sections, the markers on display bar 403 are also a visual display of the vector of CT axial slice numbers that contain a nodule.

Advantageously, the visual appearance of the markers varies with the lines with which they are associated. For example, they may have the same color as the line and that color may vary depending on whether the line joins features in the two images or the feature is found only in the first image in time or the second image in time. Alternatively, ;the marker can be a line whose length varies with the lines between the two images. For example, as in the case of markers 406, 407, 409, the marker line may be longest where the associated line joins two features in the two medical images; and as in the case of markers 408, 410, the marker line may be only half that length where the line is connected to only one feature. Further, the position of the shorter marker line may be varied to indicate whether the feature it connects to is in the first image by left-adjusting the marker as in the case of marker 408 or in the second image by right-adjusting the marker as in the case of marker 410.

Figure 5:
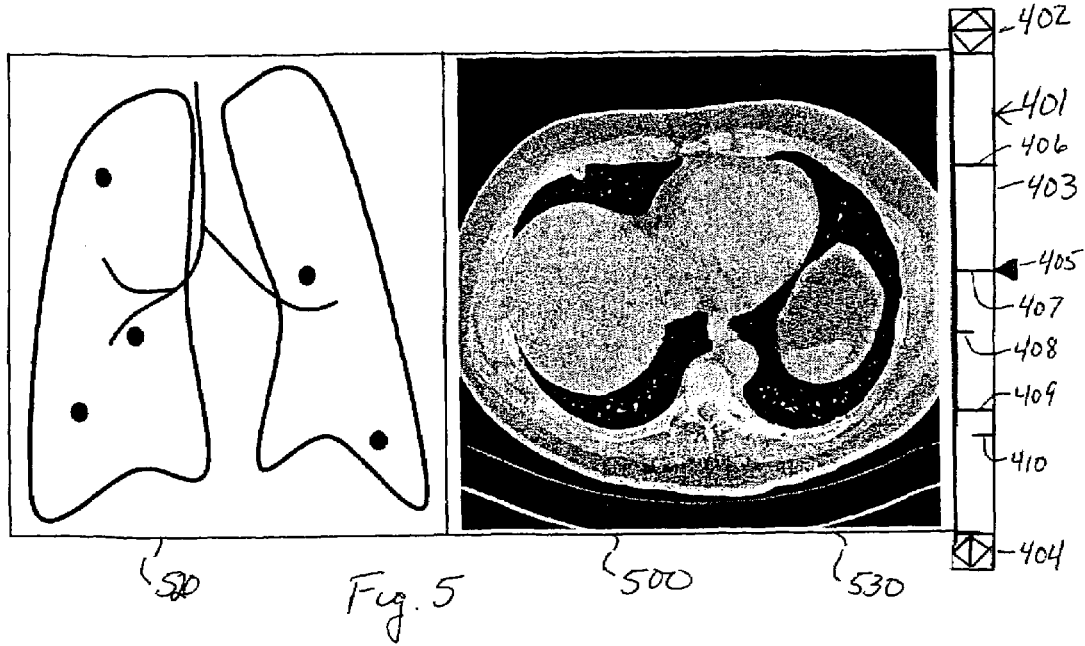
FIG. 5 is a schematic illustration of a second display in a third embodiment of the invention.

By advancing cursor 405 to a marker and clicking a mouse button or activating some other selection device, one or both axial sections associated with the corresponding line are displayed. FIG. 5 depicts such a display where the left hand image is a map 520 that locates the nodules on the lung anatomical map and the right hand image is the CT axial section 530 that displays an image of the nodule selected by the cursor 405. Preferably, map 520 is user selectable. It might be the map of the nodules in the more recent stack of CT axial sections, or the map of the nodules in the older stack, or a composite of the two maps such as that shown in FIG. 3.

The up/down scroll buttons 402 enable the user to step the display of CT sections in display 530 from one section containing a nodule to the next section containing a different nodule. Specifically, with each click of an up or down scroll button 402, display 530 goes from the display of a CT section containing one nodule to display of the CT section containing the next nodule.

Left and right scroll buttons 404 allow the user to navigate through the entire stack of CT axial sections one at a time. Each click of a left or right button changes the display 530 to display the next axial section down or up in the stack. Thus, the user is able to view the CT sections immediately adjacent to the section in which the image of the nodule appears. Alternatively, the left and right control buttons can be used to select whether the axial section that is displayed comes from the older stack of CT sections or the newer stack.

Additional controls (not shown) may also be provided to allow the user to select the images that appear alongside the scrollbar. For example, some users may prefer to have the map displayed immediately adjacent the scrollbar instead of the axial section as in FIG. 5. The user may also wish to compare an axial section in the more recent image stack with the corresponding axial section in an earlier image stack and may want to suppress display of the map to allow the display of the two sections side-by-side.

Figure 6:
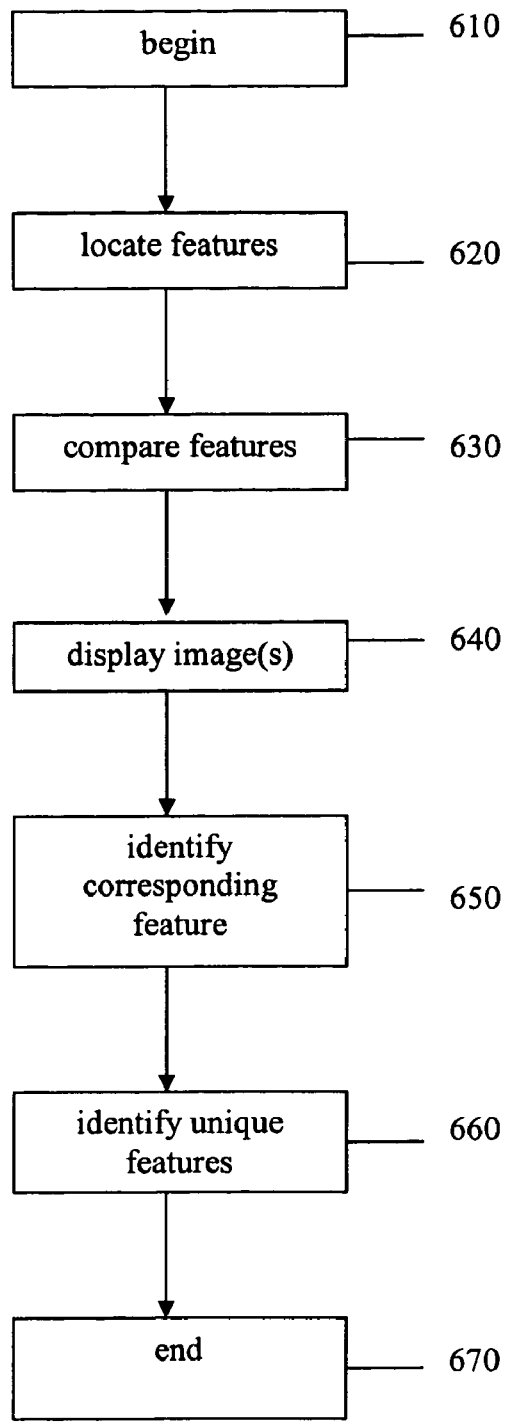
FIG. 6 is a flowchart depicting an illustrative method of the invention.

FIG. 6 is a flowchart for the software program that generates the displays of FIGS. 2-6. The software program comprises a set of computer instructions stored in a computer readable medium available to the computer that generates these displays. The program begins a step 610 with the data representing a pair of temporally related medical images. As noted above, the images may be actual images such as x-rays and the like or abstractions derived from such images such as projection maps or anatomical maps. At step 620, the program locates features or regions of interest in each of the first and second medical images. For example, in the case where the medical images are of the pulmonary region, the features might be nodules. At step 630, the program compares the two images to identify corresponding features at substantially the same location in each image. At step 640, at least one of the medical images is displayed as shown in FIG. 2 or FIG. 3. Corresponding features found in both medical images are identified at step 650; and features found in only one medical image are identified at step 660. Illustratively, as shown in FIG. 2, the corresponding features may be identified by a line connecting the corresponding features in both images and the features found in only one image may be identified by a line extending from the feature in the image where it is found toward the other feature. Where only one image is displayed as shown in FIG. 3, the features found in both images may be marked on the displayed image in one fashion while the features found in only one image may be marked in a different fashion.

As will be apparent to those skilled with the art, numerous variations may be practiced in the above-described navigational tool within the spirit and scope of the invention. Of particular note, while the invention has been described in the context of a comparison of two displays of nodules on lung anatomical background maps, it will be understood that the invention may be practiced in comparing features in other regions of the anatomy and in comparing other types of medical images. In particular, the invention may also be practiced in comparing features on actual X-ray images, sonograms, mammograms, MRI scans, CT images and the like. Moreover, the invention may be practiced to compare more than two medical images.

What is claimed is:

1. A navigational tool to facilitate the comparison of two temporally related medical images comprising:
    a display of first and second medical images alongside one another, the two images being images of the same thing at different times,
    a plurality of lines overlaying the display of the first and second medical images and extending between the images, at least a first line beginning at a feature at a first location in the first image and ending at a corresponding feature at a corresponding location in the second image and at least a second line extending from a feature found at a second location in one of the images toward a corresponding second location in the other image where no corresponding feature is found.

2. The tool of claim 1 wherein the images are images of one or both lungs and the features are nodules.

3. The tool of claim 2 wherein the first line extends from a nodule in one image to a nodule in a second image.

4. The tool of claim 2 wherein the second line extends from a nodule at a second location in the first image toward the corresponding second location in the second image where the nodule does not appear.

5. The tool of claim 2 where the second line extends from a nodule at a second location in the second image toward the corresponding second location in the first image where the nodule does not appear.

6. The tool of claim 5 further comprising a third line that extends from a nodule at a third location in the first image toward a corresponding third location in the second image where the nodule does not appear.

7. The tool of claim 6 wherein the first, second and third lines have different visual appearance.

8. The tool of claim 7 wherein the first, second and third lines have different colors.

9. The tool of claim 1 wherein the first and second lines have different visual appearance.

10. The tool of claim 1 wherein the first and second lines have different colors.

11. The tool of claim 1 further comprising a scroll bar alongside the first and second images for controlling the display of the first and second medical, the scroll bar having markers aligned with the position of the display of the first and second lines.

12. The tool of claim 11 wherein the marker aligned with the first line has different visual appearance from the marker aligned with the second line.

13. The tool of claim 12 wherein the markers are lines of different length.

14. The tool of claim 12 wherein the markers have different colors.

15. A navigational tool to facilitate the comparison of two temporally related medical images comprising:
    a display of first and second medical images alongside one another, the two images being images of the same thing at different times,
    a plurality of lines overlaying the display of first and second medical images and extending between the first and second medical images; at least a first line beginning at a feature at a first location in the first image and ending at a corresponding feature at a corresponding location in the second image and at least a second line extending from a feature found at a second location in one of the images toward a corresponding second location in the other image where no corresponding feature is found; and
    a scroll bar alongside the first and second images for controlling the display of the first and second medical, the scroll bar having markers aligned with the position of the first and second lines.

16. The tool of claim 15 wherein the images are images of one or both lungs and the features are nodules.

17. The tool of claim 15 wherein the first and second lines have different visual appearance.

18. The tool of claim 15 wherein the first and second lines have different colors.

19. The tool of claim 15 wherein the marker aligned with the first line has different visual appearance from the marker aligned with the second line.

20. The tool of claim 19 wherein the markers are lines of different length.

21. The tool of claim 19 wherein the markers have different colors.

22. A method of comparing first and second temporally related medical images comprising:

retrieving first and second medical images from a memory component, the first and second medical images being images of the same thing at different times;

locating corresponding features in each of the first and second medical images, displaying on a display device the first medical image and the second medical image along-side the first medical image, identifying on the first medical image and the second medical image the corresponding features, locating at least one feature found in one of the first or second medical images but not in the other, identifying on a displayed medical image the at least one feature found in one of the first and second medical images but not the other; and displaying on the display device a first line extending between a first feature at a first location in the first medical image and a corresponding feature at a corresponding first location in the second medical image and a second line extending from a second feature at a second location in one of the medical images toward a corresponding second location in the other image where no corresponding feature is found.

* * * * *

UNITED STATES PATENT AND TRADEMARK OFFICE
CERTIFICATE OF CORRECTION

PATENT NO.      : 7,630,531 B2
APPLICATION NO. : 11/344832
DATED           : December 8, 2009
INVENTOR(S)     : Haili Chui It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 983 days.

Signed and Sealed this

Second Day of November, 2010

David J. Kappos
*Director of the United States Patent and Trademark Office*